US008852614B2

(12) United States Patent
Frank et al.

(10) Patent No.: US 8,852,614 B2
(45) Date of Patent: Oct. 7, 2014

(54) HYDROGELS WITH NETWORK DEFECTS ENHANCED BY NANOPARTICLE INCORPORATION

(75) Inventors: Curtis W. Frank, Cupertino, CA (US); Won Jae Lee, Mountain View, CA (US); Nam-Joon Cho, Stanford, CA (US); Jeffrey S. Glenn, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 181 days.

(21) Appl. No.: 13/065,030

(22) Filed: Mar. 11, 2011

(65) Prior Publication Data
US 2011/0256183 A1  Oct. 20, 2011

Related U.S. Application Data

(60) Provisional application No. 61/340,117, filed on Mar. 12, 2010.

(51) Int. Cl.
A61K 9/00 (2006.01)
A01N 63/00 (2006.01)
C12N 5/02 (2006.01)
C12N 5/071 (2010.01)
A61K 35/12 (2006.01)
B82Y 5/00 (2011.01)
A61K 9/51 (2006.01)
A61K 38/00 (2006.01)

(52) U.S. Cl.
CPC ............... B82Y 5/00 (2013.01); C12N 5/0671 (2013.01); A61K 35/12 (2013.01); A61K 9/5184 (2013.01); C12N 2533/30 (2013.01); A61K 38/00 (2013.01); C12N 2533/40 (2013.01); Y10S 977/773 (2013.01); Y10S 977/915 (2013.01); Y10S 977/923 (2013.01)

USPC .......... 424/400; 424/93.7; 435/395; 977/773; 977/915; 977/923

(58) Field of Classification Search
CPC ..... A61K 35/12; A61K 38/00; A61K 9/5184; B82Y 5/00; C12N 2533/30; C12N 2533/40; C12N 5/0671
USPC ................. 424/400, 93.7; 977/915, 773, 923; 435/395
See application file for complete search history.

(56) References Cited

U.S. PATENT DOCUMENTS 6,886,568 B2 * 5/2005 Frondoza et al. ............. 128/898
2008/0138416 A1 * 6/2008 Rauh et al. .................... 424/488
(Continued)

OTHER PUBLICATIONS

Yanagioka et al. (Defect Generation Surrounding Nanoparticles in a Cross-Linked Hydrogel Network, Langmuir (2009) 25 (10): 5927-5939; published on line Apr. 4, 2009), 13 pages.*
Bryant; et al., "Encapsulating Chondrocytes in Degrading PEG Hydrogels With High Modulus: Engineering Gel Structural Changes to Facilitate Cartilaginous Tissue Production", Biotechnology and Bioengineering (2004), 86 (7):747-755.
(Continued)

Primary Examiner — Jason Sims
Assistant Examiner — Miriam A Levin
(74) Attorney, Agent, or Firm — Bozicevic, Field & Francis LLP; Pamela J Sherwood

(57) ABSTRACT

Compositions and methods are provided for the manufacture and use of hydrogels with increased permeability to macromolecules with minimum loss of matrix mechanical strength and prepolymer viscosity for patternability. The hydrogels of the invention are formed from a prepolymer, which is polymerized in the presence of hydrophobic nanoparticles. In some embodiments of the invention cells are present during polymerization, and are encapsulated by the hydrogel. A high interfacial energy between the hydrophobic substrate and the aqueous polymerizing solution disrupts the hydrogel network structure, leading to network defects that increase permeability without loss of patternability.

9 Claims, 8 Drawing Sheets
(4 of 8 Drawing Sheet(s) Filed in Color)

< The uniformly crosslinked ideal network>

< The actual network structure>

< The modified network structure>

(56) References Cited

U.S. PATENT DOCUMENTS

2008/0193536 A1    8/2008    Khademhosseini et al.
2009/0018033 A1    1/2009    Morgan et al.
2009/0291115 A1    11/2009    Gemeinhart

OTHER PUBLICATIONS

Cho; et al., "Viral infection of human progenitor and liver-derived cells encapsulated in three-dimensional PEG-based hydrogel", Biomed. Mater. (2009), 4(1):011001, 7pp.

* cited by examiner

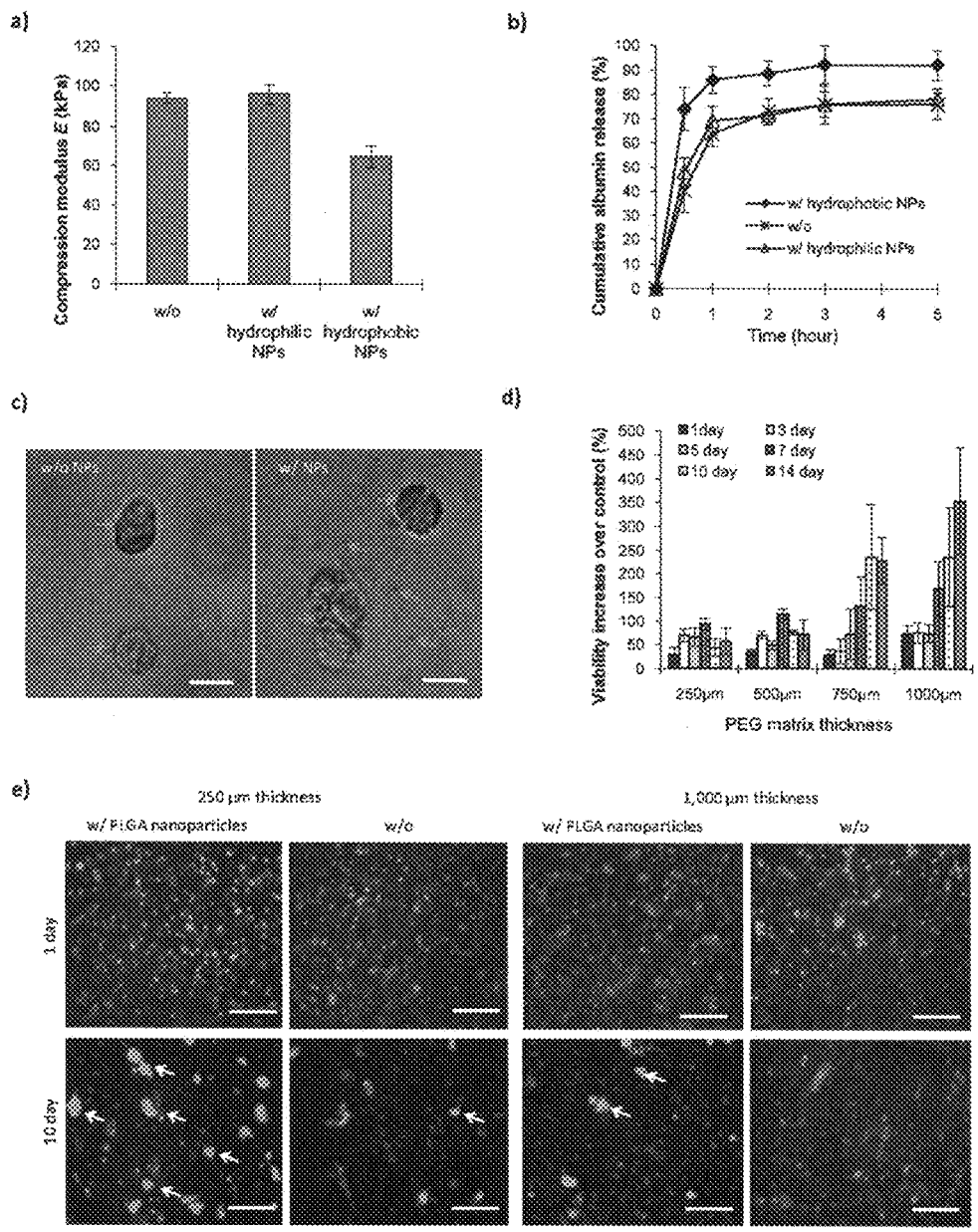

a) Effect of surface character b) Effect of degradability c) Effect of size d) Effect of NP concentration e) Effect of hydrophobicity a)

b)

c)

d)

HYDROGELS WITH NETWORK DEFECTS ENHANCED BY NANOPARTICLE INCORPORATION

BACKGROUND

Poly(ethylene glycol) (PEG) hydrogel has been successfully utilized as a cell-encapsulation material to replicate the microenvironments of various tissues. However there has been limited development of new networks with improved permeability to support metabolic activities of encapsulated cells, while maintaining patternability to recapitulate key aspects of tissue architecture.

Engineered tissues are expected to overcome shortcomings associated with traditional tissue replacement therapies and provide a platform to study various biological assays in vitro. Several types of cells cultured as two-dimensional monolayers are known to de-differentiate and lose their original functions due to disruption of their normal microenvironments. Thus, it has been a major challenge in the field of tissue engineering to provide structural and functional support equivalent to native tissues. Use of hydrogels as a scaffold material for engineered tissues has been of increasing interest due to their structural similarity to the extracellular components in the body. Photopolymerizable polyethylene glycol) (PEG) is one of the most extensively utilized hydrogels because its network structure can be easily modified to mimic critical aspects of the original microenvironments. Various approaches to design PEG networks for improved phenotype stability of encapsulated cells have involved conjugating other biologically active factors to the polymer network and incorporating degradable linkages. Another advantage of PEG is that use of photolithography or microfluidic processing allows fabrication of microarchitectures that potentially recapitulate key aspects of tissue architecture to guide cells' behavior with respect to morphology, cytoskeletal structure, and functionality (see Khademhosseini et al., Microscale technologies for tissue engineering and biology. *PNAS* 2006, 103, (8), 2480-2487).

A three-dimensional matrix of an engineered tissue needs to provide sufficient permeability to support metabolic activities, provide for unimpeded transport of large macromolecules, and permit multiple cell type interactions that are normally present in most original tissues (Sachlos et al., Making tissue engineering scaffolds work. Review: the application of solid freeform fabrication technology to the production of tissue engineering scaffolds. *Eur Cell Mater* 2003, 5, 29-39). Even though the matrix diffusion condition could be gradually improved by promoting angiogenesis or conjugating degradable linkages, it is required to allow sufficient diffusion of substances indispensable to cell survival right after cells are encapsulated. In addition, because many scaffolds for tissue engineering initially need to fill a space and provide a framework for the replaced tissue, the mechanical properties of the material are important. However, it is a challenge for hydrogel-based scaffolds to allow sufficient permeability, while maintaining mechanical properties sufficient for generating and sustaining reconstructed tissue architectures.

In many polymeric materials, improved permeability of networks has been obtained by increasing the distance between consecutive crosslinks. However, the traditional approach using higher molecular weight macromonomers to increase the distance between crosslink junctions also results in increased viscosity of the liquid phase prepolymer. This retards flow of the prepolymer solution through micro-scale architectures and also leads to decreased mechanical strength of the cured hydrogel. There have been attempts to address the relationship between the traditional polymeric parameters and the behavior of encapsulated cells in PEG networks. However, because there has been no clear explanation of the effect of cell encapsulation protocols on the PEG network structure, development of new networks has been limited.

The present invention addresses the design of networks for improved viability of the encapsulated cells. Network defects by are augmented to increase permeability. This new design has led to improved viability and function of encapsulated cells and reliable control over spatial distribution of incorporated cells at the micron-scale within cell-encapsulated three-dimensional PEG matrices.

PUBLICATIONS

US Application No. 20080193536. This application teaches cell-laden hydrogels and hydrogel assemblies thereof for use in tissue engineering. Bryant, S J, et al. (2004) Biotechnol Bioeng. 86(7):747-5 teaches encapsulating cells in degrading PEG-based hydrogels. US Application No. 20090018033 teaches crosslinking cells or proteins to PEG, and then encapsulating the PEG-crosslinked cells/proteins in PLGA. Cho, N J, et al. (2009) Biomed Mater. 4(1):11001, viral infection of human progenitor and liver-derived cells encapsulated in three-dimensional PEG-based hydrogel.

SUMMARY OF THE INVENTION

Compositions and methods are provided for the manufacture and use of hydrogels with increased permeability to macromolecules with minimum loss of matrix mechanical strength and prepolymer viscosity for patternability. The hydrogels of the invention are formed from a prepolymer, which is polymerized in the presence of hydrophobic nanoparticles. In some embodiments of the invention cells are present during polymerization, and are encapsulated by the hydrogel. A high interfacial energy between the hydrophobic substrate and the aqueous polymerizing solution disrupts the hydrogel network structure, leading to network defects that increase permeability without loss of patternability. The increased permeability translates to improved cell viability as the result of better mass transfer of gases and nutrients from the cell.

In some embodiments of the invention, a method is provided for producing cells encapsulated in a high permeability hydrogel. In such methods a hydrogel prepolymer is combined with from about 0.01% to about 1% hydrophobic nanoparticles, where the nanoparticles are from about 100 nm to about 100 μm in diameter, in the presence of cells of interest and a polymerization initiator. Generally the nanoparticles are biocompatible. Polymerization is then initiated, preferably with a photoinitiator. Optionally the prepolymer is formed into a nanostructure of interest prior to polymerization. One or a plurality of cell types may be present, where primary cells are of particular interest, including without limitation, liver cells, e.g. hepatocytes, liver endothelial cells, Kupffer cells, stellate cells, oval cells, hepatic progenitor cells, fibroblasts, and the like.

In other embodiments, an encapsulated cell composition is provided, where the cells are encapsulated in a hydrogel comprising network defects introduced by the presence of from about 0.01% to about 1% hydrophobic nanoparticles, where the nanoparticles are from about 100 nm to about 100 μm in diameter. One or a plurality of cell types may be present, where primary cells are of particular interest, including without limitation, liver cells. The hydrogel optionally comprises protein ligands, e.g. protein ligands involved in cell growth, including, without limitation, growth factors, chemokines, cytokines, fibronectin, cell adhesive peptides (RGDS), laminin, and the like. Optionally the nanoparticles comprise biologically active agents, e.g. drugs, chemokines, cytokines, growth factors, and the like. Optionally the nanoparticles are biodegradable.

In some embodiments of the invention the hydrogel provides a scaffold for cell growth, including growth of metabolically active cells, e.g. cells producing soluble products of interest, e.g. insulin, hormones, etc. The cells may be grown in vitro, e.g. a culture of one or a plurality of cell types. Cells may also be grown in vivo, e.g. where a hydrogel film provides a substrate for regenerative cell growth. The hydrogels of the invention provide appropriate mechanical strength for long term structural stability, and the viscosity of the fluid prepolymer is low enough for the prepolymer to flow into microscale structures to allow fabrication through soft lithography or microfluidic processing.

In one embodiment of the invention a system is provided for cell growth, comprising at least one hydrogel film as a substrate for cell growth. The film is optionally sterile. The system may further comprise a vessel suitable for cell growth, e.g. a flask, multi-well plate, etc., where the hydrogel film is present within the vessel.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 6:
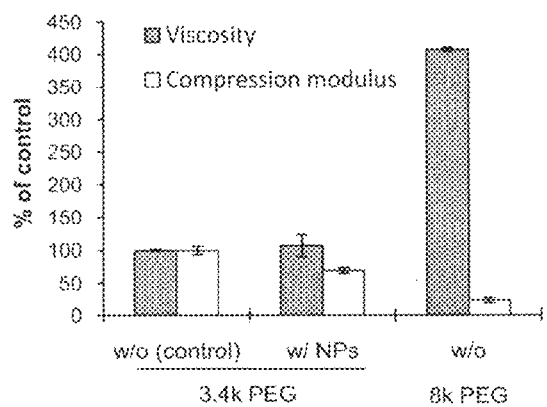
Figure 6:
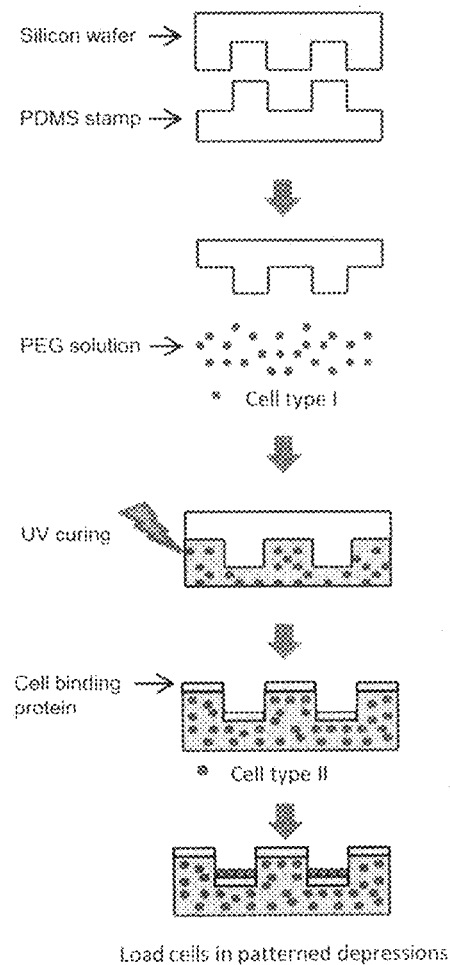
Figure 6:
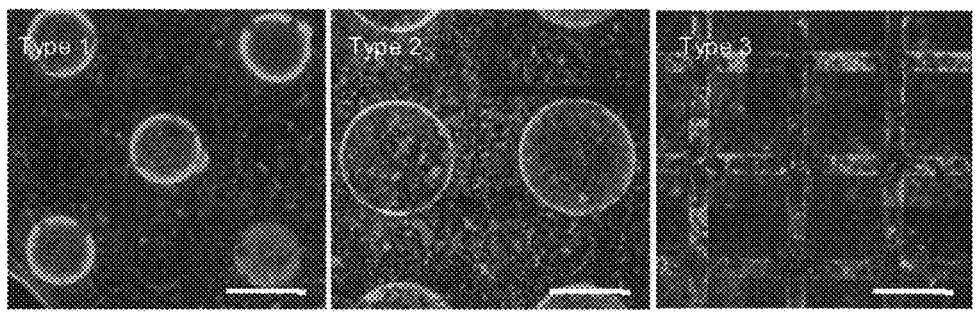
Figure 6:
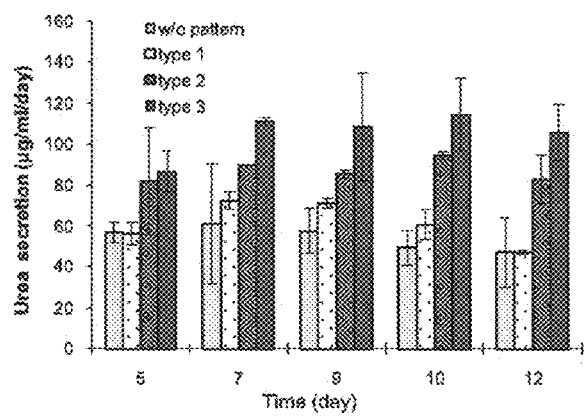

FIG. 6. (a) The addition of PLGA NPs had no significant effect on viscosity of aqueous 20% 3.4 k PEG solution (p-value>0.05), while 20% 8 k PEG had 306±3% higher viscosity that 20% 3.4 k PEG. Samples containing NPs had 31±3% reduced compression modulus than samples without NPs, while samples prepared 8 k PEG had 77±4% reduced compression modulus than samples prepared with 3.4 k PEG. (b) Schematic illustration of cell patterning process. Microstructures were fabricated in a silicon wafer by standard microfabrication techniques and then transferred to a PDMS replica. The PEG prepolymer with cells was cured between a glass slide and the PDMS replica. After depositing cell-binding proteins on the PEG surface, cells were loaded on the surface. The cells were trapped into the patterned depressions by mild agitation or flow. (c). Fluorescence images of encapsulated cells (red) in PEG matrices and patterned cells (green) on the surface. Hepatocytes and fibroblasts were encapsulated following 2 days co-culturing on cell culture dishes, and fibroblasts were loaded in the patterned depressions on the surface. All samples had the same number of encapsulated hepatocytes and fibroblasts. Type 2 and Type 3 had twice the number of fibroblasts on the surface than Type 1. Scale bar: 1.000 μm (d) As more fibroblasts on the surfaces were loaded from samples without fibroblasts to sample Type 2, urea secretions increased (p-value<0.01, Regression Analysis). Type 3 had greater urea secretion than Type 2 (p-value<0.01), even though both had the same number of fibroblasts on the surface. All statistical analyses in (d) were done after a stabilization period (from 5 day).

DESCRIPTION OF THE SPECIFIC EMBODIMENTS

Compositions and methods are provided for encapsulation of cells in a hydrogel comprising network defects introduced through the inclusion of hydrophobic nanoparticles in the prepolymer. Scaffold characteristics of interest include pore microarchitecture, swelling ratio, viscoelasticity, degradation, and cross-linking properties, which variables are designed to fall within specific parameters.

In general, cells are encapsulated within a hydrogel by mixing a cell suspension with a precursor solution comprising hydrophobic nanoparticles and crosslinking or polymerizing the resulting mixture. Any hydrophobic polymer that, upon crosslinking and/or polymerization, is capable of forming a hydrogel can be used in accordance with the present invention. In some embodiments, the percent of polymer in a precursor solution that is suitable for forming hydrogels in accordance with the present invention ranges between about 1% w/w and about 40% w/w.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Hydrogel. The term "hydrogel" refers to a three-dimensional (3D) crosslinked network of hydrophilic polymers that swell in water. Typically, cells are encapsulated within hydrogels through mixing a cell suspension with a precursor solution (i.e. a solution comprising a polymer suitable for hydrogel formation) and crosslinking the resulting network using any available means for crosslinking. In some embodiments, a plurality of hydrogels can be assembled together to form a hydrogel assembly. Included as hydrogels are polyacrylamides, hydrophilic acrylates; proteins, such as collagen, fibrin etc.; polysaccharides such as agarose, photopolymerized hyaluronic hydrogels; polyethylene glycols (PEG) and derivatives thereof, e.g. PEG-diacrylate; poly(hydroxyethyl methacrylate) (PHEMA), poly(vinyl alcohol) (PVA); and the like, as known in the art. Prepolymers may range in molecular weight depending on the specific polymer of choice. In order to evaluate the patternability, the viscosity of the prepolymer and compression modulus of the cured matrices may be measured.

In some embodiments of the invention the prepolymer is PEG or a derivative thereof, e.g. PEG diacrylate, PEG-RGD, etc. PEG hydrogels are nontoxic, non-immunogenic, inert to most biological molecules (e.g. proteins), and approved by the FDA for various clinical uses. PEG polymers can be covalently crosslinked using a variety of methods to form hydrogels. In some embodiments, PEG chains are crosslinked through photopolymerization using acrylate-terminated PEG monomers (West and Hubbell, 1995, React. Polym., 25:139). Numerous methods of modifying PEG gels are known in the art, e.g. peptide sequences have been incorporated into PEG gels to induce degradation (West and Hubbell, 1999, Macromolecules, 32:241) or modify cell adhesion (Hem and Hubbell, 1998, J. Biomed. Mater. Res., 39:266). In addition to chemical modification, block copolymers of PEG, such as triblock copolymers of PEO and poly(propylene oxide), degradable PEO, poly(lactic acid) (PLA), and other similar materials, can be used to add specific properties to the PEG hydrogels (Huh and Bae, 1999, Polymer, 40:6147). The PEG prepolymer may have a molecular weight ranging from at least about 2.5K, at least about 3.5K, at least about 5K, at least about 7.5K, at least about 10K, at least about 15K, at least about 20K and not more than about 50K. No significant differences have been found in cell viability relating to the molecular weight, although design considerations may guide the selection of a prepolymer.

The percent of hydrogel prepolymer in a precursor solution may range from at least about 7.5%, at least about 10%, at least about 15%, at least about 20%, at least about 30%, and usually not more than about 40%.

During the course of the methods of the invention, the prepolymer will generally by polymerized or cross-linked, depending on the specific hydrogel. Any crosslinking method known in the art can be utilized, including, but not limited to, photocrosslinking, chemical crosslinking mechanisms, physical crosslinking mechanisms, irradiative crosslinking mechanisms, thermal crosslinking mechanisms, ionic crosslinking mechanisms, and the like.

Initiators that maintain the viability of the cells are preferred, particularly photoinitators where hydrogels can be photopolymerized in the presence of photoinitiators via exposure to ultraviolet (UV) light (Scranton and Bea, Photopolymerization fundamentals and applications, ACS Publishers, 1996). Polymers that can be crosslinked using photocrosslinking include, but are not limited to, polysaccharide based hydrogels (e.g. hyaluronic acid, chitosan, dextran, etc.), PEG-diacrylate, etc. Any photoinitiator may be used in the crosslinking and/or polymerization reaction. Photoinitiated polymerizations and photoinitiators are discussed in detail in Rabek, Mechanisms of Photophysical Processes and Photochemical Reactions in Polymers, New York: Wiley & Sons, 1987; Fouassier, Photoinitiation, Photopolymerization, and Photocuring, Cincinnati, Ohio: Hanser/Gardner; Fisher et al., 2001, Annu. Rev. Mater. Res., 31:171.

A photoinitiator may be designed to produce free radicals at any wavelength of light. In certain embodiments, the photoinitiator is designed to work using UV light (200-500 nm). In certain embodiments, long UV rays are used. In other embodiments, short UV rays are used. In some embodiments, a photoinitiator is designed to work using visible light (400-800 nm). In certain embodiments, a photoinitiator is designed to work using blue light (420-500 nm). In some embodiments, the photoinitiator is designed to work using IR light (800-2500 nm). The output of light can be controlled to provide greater control over the crosslinking and/or polymerization reaction. Light may be applied to a precursor solution for about 10 seconds to about 5 minutes. In certain embodiments, light is applied for about 10 to about 60 seconds. In some embodiments, light is applied for about 10 to about 30 seconds. In some embodiments, light is applied for about 20 to about 40 seconds. The light source may allow variation of the wavelength of light and/or the intensity of the light. Light sources useful in the inventive system include, but are not limited to, lamps, fiber optics devices, etc.

In certain embodiments, the photoinitiator is acetophenone; diphenyl(2,4,6-trimethylbenzoyl)phosphine oxide; 4,4'-dimethoxybenzoin; anthraquinone; anthraquinone-2-sulfonic acid; benzene-chromium(0) tricarbonyl; 4-(boc-aminomethyl)phenyl isothiocyanate; benzil; benzoin; benzoin ethyl ether; benzoin isobutyl ether; benzoin methyl ether; benzophenone; benzoic acid; benzophenone/1-hydroxycyclohexyl phenyl ketone, 50/50 blend; benzophenone-3,3',4,4'-tetracarboxylic dianhydride; 4-benzoylbiphenyl; 2-benzyl-2-(dimethylamino)-4'-morpholinobutyrophenone; 4,4'-bis(diethylamino)benzophenone; Michler's ketone; (.+–.)-camphorquinone; 2-chlorothioxanthen-9-one; 5-dibenzosuberenone; 2,2-diethoxyacetophenone; 4,4'-dihydroxybenzophenone; 2,2-dimethoxy-2-phenylacetophenone; 4-(dimethylamino)benzophenone; 4,4'-dimethylbenzil; 3,4-dimethylbenzophenone; diphenyl(2,4,6-trimethylbenzoyl) phosphine oxide/2-hydroxy methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methyl benzoylformate; 2-methyl-4'-(methylthio)-2-morpholinopropiophenone; 9,10-phenanthrenequinone; 4'-phenoxyacetophenone; thioxanthen-9-one; triarylsulfonium hexafluorophosphate salts; 3-mercapto-1-propanol; 1'-mercapto-1-undecanol; 1-mercapto-2-propanol; and 3-mercapto-2-butanol, all of which are commercially available from Sigma-Aldrich. In certain embodiments, the free radical initiator is selected from the group consisting of benzophenone, benzyl dimethyl ketal, 2-hydroxy-2-methyl-phenylpropanone; 2,4,6-trimethylbenzoyldiphenyl phosphine oxide; 2,4,6-trimethyl benzophenone; oligo(2-hydroxy-2-methyl-1-(4-(1-methylvinyl)phenyl)propanone and 4-methylbenzophenone. In certain embodiments, the photoinitiator is dimethoxy-2-phenyl-acetophenone (DMPA). In certain embodiments, the photoinitiator is a titanocene. In certain specific embodiments, the photoinitiator is 2-hydroxy-1-(4-(hydroxyethoxy)phenyl)-2-methyl-1-propanone. In certain specific embodiments, the photoinitiator is Igracure. In certain embodiments, a combination of photoinitiators is used.

Hydrophobic nanoparticle. Nanoparticles used in the methods of the invention are comprised of any suitable, biocompatible, hydrophobic material. The hydrophobicity may be measured by water contact angle. Nanoparticles of interest are usually at least about 100 nm diameter, and may be at least about 250 nm, at least about 500 nm, at least about 1 μm, at least about 10 μm, and not more than about 100 μm in diameter. The composition of the nanoparticle is such that it has no accessible chemistry to react with the polymer, and does not participate in the cross-linking or polymerization of the polymer.

Suitable materials for nanoparticles include, without limitation, poly-lactic acid (PLA), poly-glycolic acid (PLG), poly (lactic-co-glycolic acid) (PLGA), polystyrene, poly(dimethylsiloxane) (PDMS), etc. Any suitable method of preparing the particles may be used, e.g. spontaneous emulsification solvent diffusion method (Niwa et al. (1993) J. Controlled Release 25(1-2):89-98), cross-linking, polymerization as described above, and the like.

Nanoparticles are added to a precursor solution comprising the prepolymer at a concentration of at least about 0.01% w/w, at least about 0.05%, at least about 0.1%, at least about 0.5%, at least about 1%, and not more than about 2.5%.

Biocompatible: As used herein, the term "biocompatible" refers to substances that are not toxic to cells. In some embodiments, a substance is considered to be "biocompatible" if its addition to cells in vitro results in less than or equal to approximately 10% cell death, usually less than 5%, more usually less than 1%. In some embodiments, a substance is considered to be "biocompatible" if its addition to cells in vivo does not induce inflammation and/or other adverse effects in vivo. The term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

Cells. The hydrogel films of the invention provide a substrate for cell viability and growth, which may be vertebrate cells, e.g. mammalian cells, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human. The cells which are employed may be fresh, frozen, or have been subject to prior culture. They may be fetal, neonate, adult. The cells may be primary cell cultures, cell lines, cells present in an animal, etc.

In general, the cells should be viable when encapsulated within hydrogels. Exemplary cells that can be encapsulated within hydrogels include stem cells, totipotent cells, pluripotent cells, and/or embryonic stem cells. In some embodiments, exemplary cells that can be encapsulated within hydrogels in accordance with the present invention include, but are not limited to, primary cells and/or cell lines from any tissue. For example, cardiomyocytes, myocytes, hepatocytes, keratinocytes, melanocytes, neurons, astrocytes, embryonic stem cells, adult stem cells, hematopoietic stem cells, hematopoietic cells (e.g. monocytes, neutrophils, macrophages, etc.), ameloblasts, fibroblasts, chondrocytes, osteoblasts, osteoclasts, neurons, sperm cells, egg cells, liver cells, epithelial cells from lung, epithelial cells from gut, epithelial cells from intestine, liver, epithelial cells from skin, etc., and/or hybrids thereof, may be encapsulated within hydrogels in accordance with the present invention. In this respect, the cells can be autogenic, allogenic or xenogenic with respect to a subject receiving the hydrogel.

The cells may be regenerative, that is they give rise to new cells and tissues, e.g. as stem cells, progenitor cells, lineage committed progenitor cells, and the like. Fibroblasts and other epithelial precursor cells may also be included. The term stem cell is used herein to refer to a cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Cells may be initially seeded or grown on the hydrogel in vitro, where the hydrogel is placed in a suitable vessel for culture, e.g. a flask, plate, multiwell plate, etc. The cells are grown in vitro in an appropriate liquid nutrient medium. Generally, the seeding level will be at least about 10 cells/ml, more usually at least about 100 cells/ml and generally not more than about $10^5$ cells/ml, usually not more than about $10^4$ cells/ml.

Any cell culture medium appropriate for growth and differentiation of cells may be used in cell cultures employing the present collagen cell culture substrates. These include, but are not limited to, DMEM, MEM, M-199 and RPMI. Supplements, as are known in the art, may be added to the culture medium and include serum (e.g., FBS or calf serum), serum-containing supplements (N IU-SERUM), and serum-free supplements (MITO+).

Those skilled in the art will recognize that the cells listed herein represent an exemplary, not comprehensive, list of cells that can be encapsulated within a precursor solution (and, therefore, eventually in a hydrogel) in accordance with the present invention.

Factors. Polypeptide growth factors and cell-signalling molecules may be included in the hydrogel. Protein ligands can be printed on the hydrogels by micro-contact printing methods. Alternatively the proteins may be included in the initial fabrication of the matrix. Polypeptides of interest as growth factors include, without limitation, the following molecules, where one or more of the factors may be patterned on a matrix. The native form of the polypeptides may be used, or variants thereof, e.g. truncated versions that maintain biological activity; stabilized variants; conjugated engineered for improved adhesion to the hydrogel matrix, and the like.

Platelet-derived growth factor (PDGF) is a family of potent activators for cells of mesenchymal origin, and a stimulator of chemotaxis, proliferation and new gene expression in monocytes, macrophages and fibroblasts, accelerating ECM deposition. This family of growth factors exists in both homo- and heterodimeric forms.

Cytokines of the transforming growth factor-β family (TGF-β) are multifunctional regulators of cell growth, differentiation and ECM formation. In mammals, there are three isoforms, TGF-β1, TGF-β2 and TGF-β3. In particular, in relation to wound healing in the skin, TGF-β1 and TGF-β2 are implicated in cutaneous scarring, whereas TGF-β3 is known to have an anti-scarring effect.

Bone morphogenetic proteins (BMPs) are members of the TGF-β superfamily. There are 15 members and although they are known for their role in bone and cartilage formation, they have diverse roles in many other developmental processes.

Fibroblast growth factors (FGFs) are a family of 21 isoforms with a broad spectrum of activities, including regulation of cell proliferation, differentiation and migration. FGFs 1, 2, 5, 7 and 10 are upregulated during adult cutaneous wound healing. bFGF may have the ability to accelerate tissue regeneration in artificial dermis.

Vascular endothelial growth factor (VEGF) is induced during the initial phase of skin grafting, where endogenous fibrin clots are known to form a provisional matrix and to promote angiogenesis. Growth factors such as VEGF increase in such wounds to stimulate angiogenesis.

Epidermal growth factor (EGF) has been implicated in wound healing and homeostasis in a number of tissues.

Hepatocyte growth factor/scatter factor (HGF/SF) is a pleiotrophic growth factor produced principally by cells of mesenchymal origin. HGF has been implicated in enhancing the cutaneous wound healing processes of re-epithelialization, neovascularization and granulation tissue formation.

The hydrogels may further comprise antimicrobial agents and other drugs. Agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Antiviral agents, e.g. acyclovir, gancyclovir, etc. may also be included.

Supports. A variety of solid supports or substrates may be used with the hydrogel, including deformable. By deformable is meant that the support is capable of being damaged by contact with a rigid instrument. Examples of deformable solid supports include polyacrylamide, nylon, nitrocellulose, polypropylene, polyester films, such as polyethylene terephthalate; PDMS (polydimethylsiloxane); etc. as known in the art for the fabrication of wound dressings. Examples of non-deformable supports include glass or silicon supports.

Photolithography (Koh et al., 2003, Anal. Chem., 75:5783; Liu and Bhatia, 2002, Biomed. Microdev., 4:257; and Koh et al., 2002, Langmuir, 18:2459) and soft lithography (Tang et al., 2003, J. Am. Chem. Soc., 125:12988) may be used to encapsulate cells within small units of polymeric hydrogels anchored onto two-dimensional (2D) surfaces. For example a soft lithography approach can be used to control the geometry and dimensions of encapsulated cells in PEG matrices, where a desired microstructure may be fabricated in a silicon wafer and transferred it to a poly(dimethylsiloxane) (PDMS) replica, where the cell-containing PEG prepolymer is cured between the PDMS replica and a glass slide. Structures of interest include microfluidic channels, where the walls of microchannels are made from hydrogels.

In some embodiments, it is desirable that cells are evenly distributed throughout a hydrogel. In some embodiments, cells are located on the surface of a hydrogel. In some embodiments, cells are located in the interior of a hydrogel. In some embodiments, cells are layered within a hydrogel. In some embodiments, each cell layer within a hydrogel contains different cell types. In some embodiments, cell layers within a hydrogel alternate between two cell types.

In some embodiments, the conditions under which cells are encapsulated within hydrogels are altered in order to maximize cell viability. In some embodiments, for example, cell viability increases with lower polymer concentrations, lower photoinitiator concentration, and shorter UV exposure times. Cell viability can be measured by one of many indicators of cell viability, including intracellular esterase activity, plasma membrane integrity, metabolic activity, gene expression, and protein expression. For liver cells, metabolic activity such as the production of urea may be monitored, as described in the examples. The hydrogels of the invention provide for improved cell viability, e.g. where after a period of 1 day the cell viability is improved at least about 10% when compared to a comparable hydrogel not formed with hydrophilic nanoparticles, improved at least about 25%, improved at least about 50%, and may be improved at least about 75%, 80%, 90% or more.

The concentration of cells in a precursor solution is usually at least about $1\times10^4$ cells/ml, at least about $1\times10^5$ cells/ml, at least about $1\times10^6$ cells/ml, at least about $1\times10^7$ cells/ml and not more than about $1\times10^8$ cells/ml.

The population of cells in a hydrogel or assembly of hydrogels In some embodiments, a single hydrogel comprises a population of identical cells and/or cell types. In some embodiments, a single hydrogel comprises a population of cells and/or cell types that are not identical. In some embodiments, a single hydrogel may comprise at least two different types of cells. In some embodiments, a single hydrogel may comprise 3, 4, 5, 10, or more types of cells. Alternatively a single hydrogel may comprise a single cell type, but be layered with a hydrogel comprising a different cell type.

Devices and Methods

Cells are encapsulated within a hydrogel by mixing a cell suspension with a precursor solution as described above and crosslinking or polymerizing the resulting mixture. In accordance with the present invention, a precursor solution comprises one or more polymers and/or polymer precursors (e.g., monomers, oligomers, etc.) and one or more cells. Cells encapsulated in hydrogels and/or hydrogel assemblies in accordance with the present invention may be used for various cell culture and tissue engineering applications. In some embodiments, tissue engineering aims to replace, repair, and/or regenerate tissue and/or organ function or to create artificial tissues and organs for transplantation. In general, scaffolds used in tissue engineering (e.g. hydrogel scaffolds) mimic the natural extracellular matrix (ECM) and provide support for cell adhesion, migration, and proliferation.

Hydrogels comprising cells and/or precursor solutions for hydrogel formation may be administered by any route, usually local or topical introduction. The cell containing hydrogels can be used for the treatment and/or diagnosis of various conditions requiring the presence of viable cells. Subjects include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys. In some embodiments, tissue engineering aims to replace, repair, and/or regenerate tissue and/or organ function or to create artificial tissues and organs for transplantation.

In some embodiments the cell containing hydrogels are used for tissue-engineering applications; including growth of bone, cartilage, vascular tissues, cardiac tissues, endocrine glands, liver, renal tissue, lymph nodes, pancreas, and other tissues. Liver cells and restoration of liver function is of particular interest.

The present invention provides precursor solutions or cured hydrogels comprising cells, at least one polymer, hydrophobic nanoparticles; and one or more pharmaceutically acceptable excipients. Such pharmaceutical compositions may optionally comprise one or more additional therapeutically-active substances. In accordance with some embodiments, a method of administering such a pharmaceutical composition to a subject in need thereof is provided.

Pharmaceutically acceptable excipients include solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21.sup.st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator. General considerations in the formulation and/or manufacture of pharmaceutical agents may be found, for example, in Remington: The Science and Practice of Pharmacy 21.sup.st ed., Lippincott Williams & Wilkins, 2005.

The invention provides a variety of kits comprising one or more of the hydrogels or precursors thereof. A kit may include, for example, (i) a precursor solution comprising a cell, a hydrophobic nanoparticle, a polymer, and a crosslinking initiator; and (ii) instructions for forming a hydrogel from the precursor solution. In some embodiments, a kit may include, for example, (i) a plurality of microgels, each comprising a cell and at least one polymer.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

Hydrophobic Nanoparticles Improve Permeability of Cell-encapsulated Poly(Ethylene Glycol) Hydrogels while Maintaining Patternability The viability of encapsulated liver-derived cells has been shown to be susceptible to the encapsulating matrix diffusion condition, and so we utilized human liver-derived cells as a model to evaluate the structure of cell-encapsulated PEG networks. We used immortalized Huh 7.5 cells to optimize cell-encapsulating conditions, which were subsequently applied to human primary hepatocytes. In this study, we show that the optimized protocol for cell encapsulation leads to formation of network defects, and that the level of network defects is the appropriate spatial feature to address permeability in designing the network. This understanding led us to augment the level of network defects by incorporating hydrophobic poly(lactic-co-glycolic acid) (PLGA) nanoparticles (NPs) within the hydrophilic PEG network; we have verified that this modification improves hydrogel permeability with minimum loss of patternability. Our new network design leads to improved viability and functions of encapsulated human liver-derived cells and has the structural advantage of supporting micron-scale architectures for control of the spatial distribution of the incorporated cells.

The level of network defects is a major determinant of permeability for cell-encapsulated PEG networks. We first attempted to identify the critical design parameters of the PEG network that influence the encapsulated cell viability. As a reference sample, we used 3.4 k molecular weight of PEG and prepared samples from prepolymer with 20% (w/w) solid content, referred to as 20% 3.4 k PEG. In order to focus on the relationship of the PEG network to the viability of encapsulated liver-derived cells, photopolymerization parameters were optimized to obtain maximum cell viability. This involved reducing the photoinitiator concentration, UV exposure time, and UV intensity (Bryant et al. (2000) J. Biomater. Sci., Polym. Ed. 11 (5), 439-457). These minimum curing conditions led to lower crosslinking density and more network defects than samples prepared under much more complete curing conditions (Myung et al. (2007) Polymer 48(18), 5376-5387), as inferred from the significantly reduced mechanical strength of samples cured under conditions that were optimized for improved cell viability (FIG. 1a).

Figure 1:
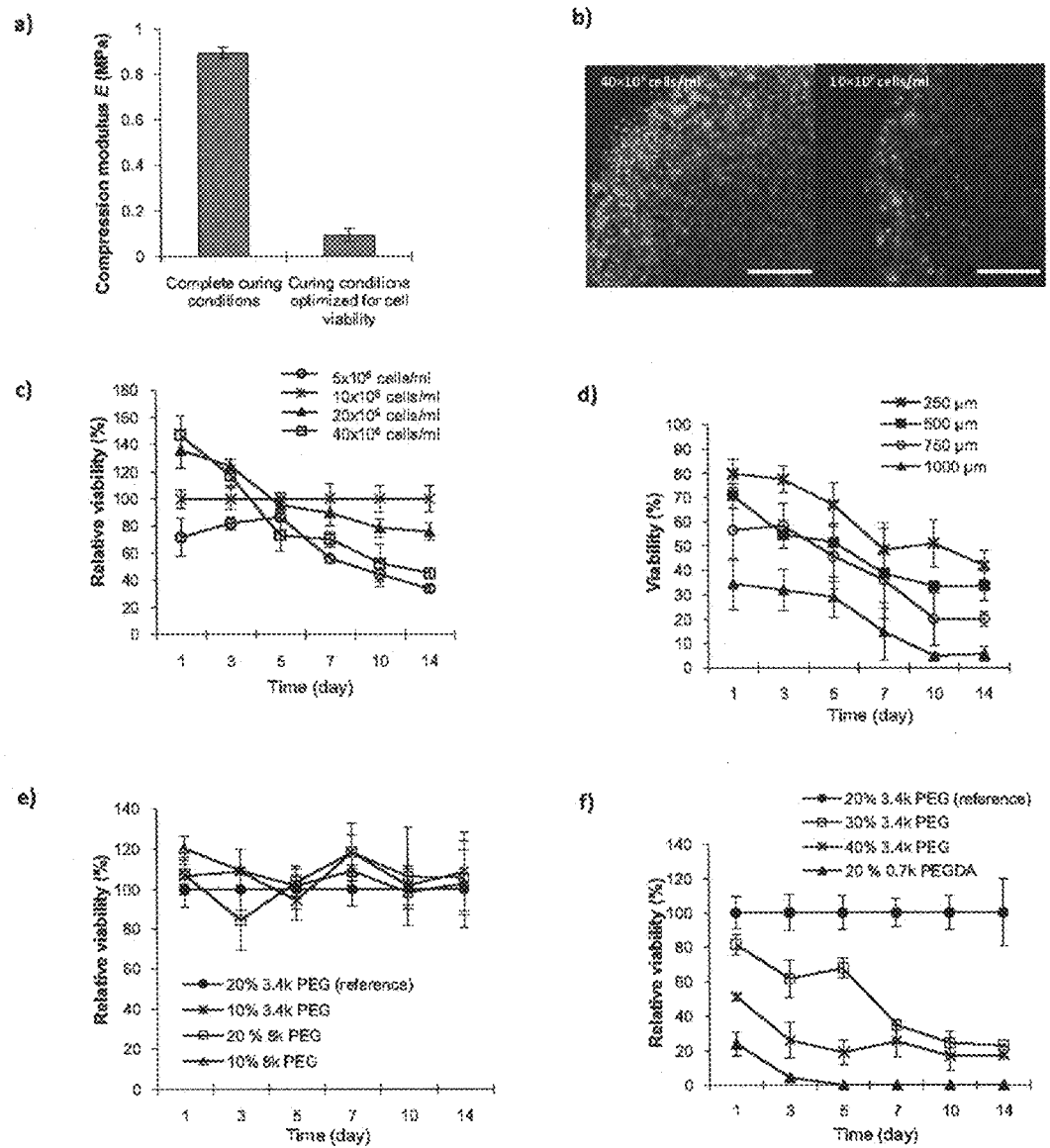
FIG. 1. (a) Compression modulus comparison between samples (20% 3.4 k PEG) cured under conditions optimized to improve the viability of encapsulated cells (UV (320-390 nm wavelength) 50 second exposure time, 0.05% (w/v) photoinitiator (P.I.) concentration) and a complete curing condition (10 min UV exposure time, 1% (w/v) P.I. concentration) (b) The cells encapsulated in 250 μm thickness matrices were stained by Live/Dead® assay (green: live cells, red: dead cells). The top view images were taken in the middle portion of the overall thickness. The viability at the edge of the PEG matrix is higher than in the middle part at $40 \times 10^6$ cells/ml density (Scale bar: 200 μm). This difference could be ignored at $10 \times 10^6$ cells/ml density. (c) Increase of cell density to more than $10 \times 10^6$ cells/ml led to improved viabilities, but only in the short term. As the incubation period increased, there were faster viability drops than for samples with $10 \times 10^6$ cells/ml density. (d) Huh 7.5 cells were encapsulated in different thicknesses of PEG matrices at $10 \times 10^6$ cells/ml density. The survival of the encapsulated cells depended strongly on the diffusion conditions of the matrices, which was confirmed by correlation between cell viabilities and matrix thicknesses (p-value<0.0001, Regression Analysis). (e) When samples were prepared by increasing molecular weight or reducing solid content from 20% 3.4 k PEG, there were no significant changes in the viability of encapsulated cells compared with 20% 3.4 k PEG (for all samples, p-value>0.5) (f) However, there were significant cell viability drops from 20% 3.4 k PEG to 30% 3.4 k PEG (p-value<0.01), from 30% 3.4 k PEG to 40% 3.4 k PEG (p-value<0.01), and 20% 3.4 k PEG to 20% 0.7 k PEG (p-value<0.01).

A notable feature of the Huh 7.5 cells encapsulated in the reference PEG matrices was that the cell viability was always greater at the edges of the PEG disc than in the middle portion, but this became less pronounced as the encapsulated cell density decreased (FIG. 1b). Since cells with higher density require more diffusion of nutrients, oxygen, and waste-by-products per unit of surface area of the PEG matrices to support their metabolic activities, we hypothesized that lower cell viability in the middle portion was caused by insufficient permeability of the PEG hydrogel. In particular, the effect of oxygen supply has been established as a critical factor for survival and function of liver-derived cells. We also found that samples with higher cell density had better overall viability, but only in the short term (FIG. 1c). Thus, the initial viability increase for high cell density was caused by enhanced cellular interaction offered by reduced intercellular distances; however, the PEG network could not maintain this benefit for a long period due to its limited permeability. We also confirmed the need to improve the permeability from the observation that increasing the thickness of the PEG hydrogel led to decreased viabilities in both Huh 7.5 cells (FIG. 1d, p-value<0.0001, Regression Analysis) and human fetal primary hepatocytes.

As a first step to improve the permeability, we increased the molecular weight of the PEG macromonomers to 8 k and reduced the solid content in the prepolymer from 20% (w/w) to 10% (w/w), because this will increase the distances between the consecutive crosslinks and improve the permeability. However, we did not observe improved viability of encapsulated Huh 7.5 cells when we changed either the macromonomer molecular weight or the solid content, as shown in FIG. 1e. Similar results were reported in a previous study (Underhill et al. (2007) Biomaterials 28(2):256-270) in which there were no significant differences in viabilities for mouse liver-derived cells encapsulated in 3.4 k and 20 k PEG. These data indicate that better permeability from the cell-encapsulated 20% 3.4 k PEG matrices cannot be achieved simply by increasing distances between consecutive crosslinks in the polymeric networks. Interestingly, there were decreased viabilities when the solid content increased from 20% up to 40% or the molecular weight decreased from 3.4 k to 0.7 k (FIG. 1f), which implies that the permeability of PEG matrices could be affected by these parameters. These data are in contrast to the previous work on the permeability of PEG matrices without encapsulated cells, in which the diffusion of various biomolecules was reported to be sensitively regulated when average distances of consecutive crosslinks were modulated by macromonomer molecular weight and solid content.

We encapsulated cells into PEG matrices and added virus particles into the cell culture medium. Then we observed that encapsulated liver-derived cells could be infected with hepatitis C and pseudotyped lentiviruses, and the progeny of the viruses could be recovered from the media supernatants (Cho et al. (2009) Biomed Mater 4(1):11001-11007). The sizes of the hepatitis C virus (HCV) and the lentivirus particles are 50 nm and 100 nm, respectively. However, when the possible distances between consecutive crosslinks are roughly estimated from uniformly crosslinked networks of 3.4 k or 8 k PEG, they cannot exceed 5 nm. We hypothesized that the cell-encapsulating PEG networks had numerous network defects large enough for the virus particles to successfully penetrate and infect the cells. Therefore, network defects appear to provide a major pathway for solute diffusion, such that the overall permeability would not be expected to be substantially affected by designing the network to have increased distances between the consecutive cross-links. From FIG. 1e, we infer that samples with increased molecular weight or decreased solid content seemed to have similar levels of network defects as the 20% 3.4 k PEG network. The decreased viability from 20% 3.4 k PEG to samples prepared by increasing solid content or decreasing molecular weight in FIG. 1f implies that fewer network defects were produced during polymerization, and the distances between consecutive crosslinks determined the overall network permeability. Based on this understanding of the cell-encapsulated PEG network, we sought to augment the level of network defects to improve further the permeability.

Figure 2:
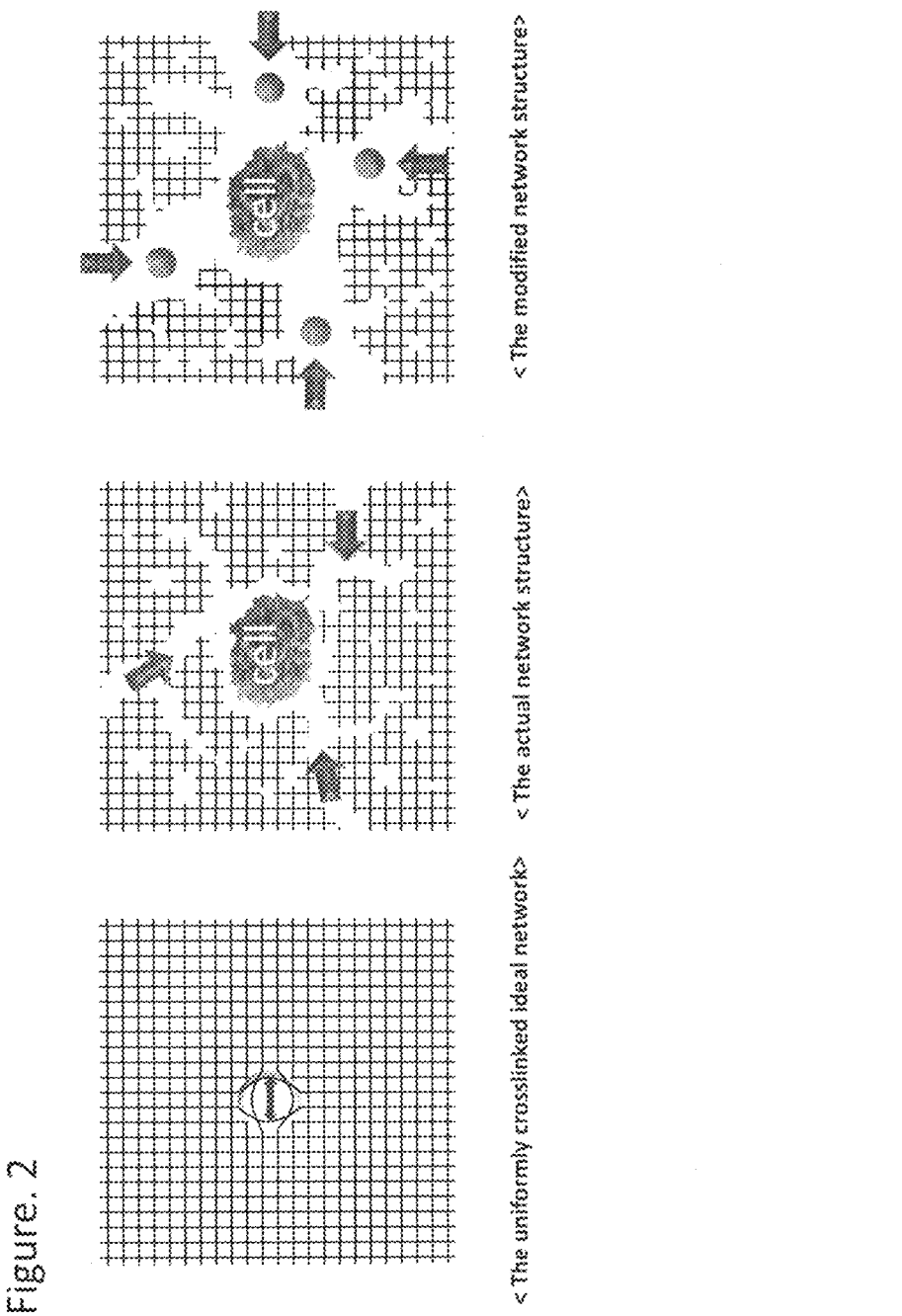
FIG. 2. The distances between consecutive crosslinks (red arrow) control the permeability of polymeric networks only in the case when the network is uniformly crosslinked. However, under the curing condition optimized for cell-encapsulated PEG networks, there are numerous network defects (blue arrows), which appear to be up to orders of magnitude larger than the possible range of distances between consecutive crosslinks. Therefore, the level of these network defects is the primary determinant of the hydrogel permeability and its consequent ability to support metabolic activities of encapsulated cells. These network defects could be augmented by the incorporation of hydrophobic NPs (green circles), which are believed to induce even looser crosslinking within the hydrophilic PEG network.

Augmentation of network defects by incorporating hydrophobic nanoparticles improves the phenotype stability of encapsulated cells. It has been reported that hydrogels cured in contact with hydrophobic surfaces exhibit-characteristics attributed to lower crosslinking density than hydrogels cured on hydrophilic glasses (Gong et al. (2001) J. Am. Chem. Soc. 123(23):5582-5583. The major driving force for inhomogeneous gelation adjacent to a hydrophobic surface was thought to be the high interfacial energy between the hydrophobic substrate and the aqueous polymerizing solution. Thus, in an attempt to further disrupt the PEG network structure so as to increase its permeability, we incorporated hydrophobic nanoparticles (NPs) into the hydrogel matrix. By analogy, the large interfacial zone between the hydrophobic particles and the surrounding aqueous macromonomer solution should lead to a higher degree of network defects in the vicinity of the particles (FIG. 2).

Figure 3:
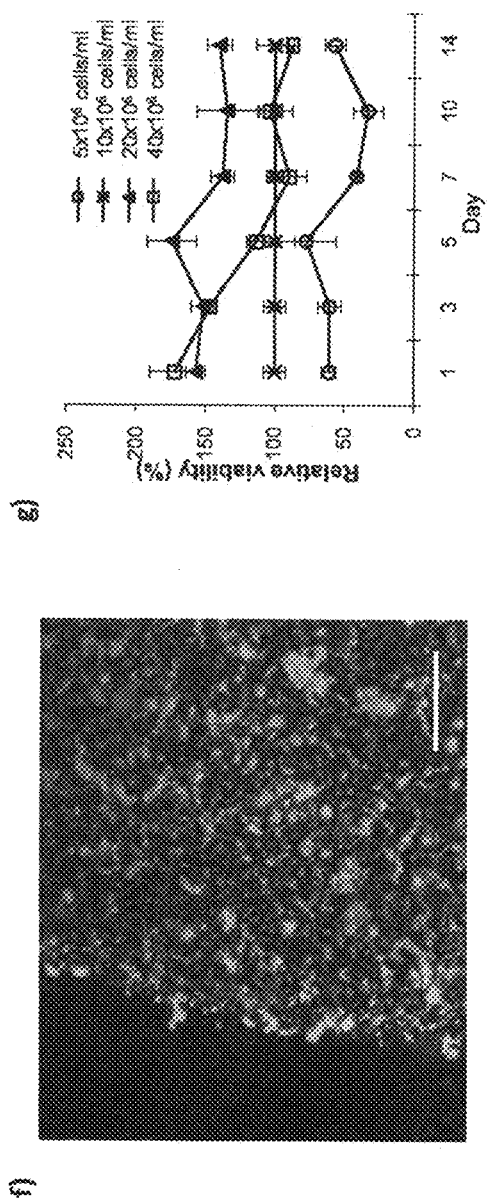
FIG. 3. (a) Compression modulus of PEG matrices without NPs, with hydrophilic NPs, or with hydrophobic PLGA NPs were measured, and only hydrophobic NP-containing samples had reduced compression modulus (p-value<0.01). (b) When albumin was encapsulated in PEG matrices without cells, samples containing hydrophobic PLGA NPs showed significantly improved albumin release, (p-value<0.01), while hydrophilic NPs had no effect on release profiles (p-value>0.05), compared with samples without NPs. (c) PLGA NPs (red arrows) were incorporated within matrices encapsulating Huh 7.5 cells (green arrows). Scale bar: 10 μm. (d) For different thicknesses of PLGA NP-containing samples, increased cell viabilities were observed compared with samples without NPs. (e) The improved viabilities in NP-containing samples are shown in the figures stained by Live/Dead® assay (green: live cells, red: dead cells). White arrows indicate cell colonies resulting from individual cells' proliferation. Scale bar: 100 μm. (f) When PLGA NPs were incorporated, the difference in cell viabilities between the edge and middle portions of the matrices was reduced at $40 \times 10^6$ cells/ml cell density. Scale bar: 300 μm. (g) With incorporated PLGA NPs, the PEG network can support a higher cell density, i.e., $20 \times 10^6$ cell/ml, while samples without NPs had the optimal cell density of $10 \times 10^6$ cell/ml, as shown in FIG. 1b.

We first evaluated whether the incorporated hydrophobic NPs would augment network defects and improve permeability. We selected poly(lactic-co-glycolic acid) (PLGA) as a suitable hydrophobic material for the particle because of its biocompatibility. Moreover, because PLGA particles have been developed as drug carriers, they could also be used to deliver various biological factors to guide the behavior of cells incorporated. When hydrophobic NPs (870±34 nm diameter) were incorporated into PEG matrices (0.01% w/v) without cells, we observed reduced mechanical strength (FIG. 3a), indicating that the level of network defects had increased; however, no change was observed when hydrophilic NPs (785±6 nm diameter) were added (FIG. 3a, p-value>0.05). Since albumin (14×4×4 nm$^3$ dimensions) is known to be an effective marker to probe effective network sizes, we also compared albumin release from samples with hydrophobic NPs with release results for samples containing hydrophilic NPs. We observed that only hydrophobic NPs improve the permeability of PEG matrices (FIG. 3b, p-value<0.01); no such effect was observed for hydrophilic NP-containing samples (FIG. 3b, p-value>0.05).

We then incorporated PLGA NPs into cell-encapsulated PEG matrices. FIG. 3c depicts Huh 7.5 cells encapsulated in PEG matrices with and without the hydrophobic NPs. Cell viability was increased for all the different thicknesses of PLGA NP-containing samples, as shown in FIG. 3d. The increasing cell viability in proportion to the matrix thickness implies that the dominant benefit from addition of PLGA NPs is the improvement in permeability. FIG. 3e shows a significant increase in the live cell population (green fluorescence) and in the number of cell colonies (white arrows) for the PLGA NP-containing samples, as stained by the Live/Dead® viability measurement kit. The formation of cell colonies is important for hepatic cells to function normally because of their dependence on cellular interaction. Thus, our new network design provides a more desirable environment for encapsulated cells to proliferate and restore homotypic cellular interaction. We also observed improved cell viability in the middle of PEG matrices at 40×10$^6$ cells/ml density (FIG. 3f). The optimal cell density of Huh 7.5 cells in 20% 3.4 k PEG matrices was increased from 10×10$^6$ cells/ml to 20×10$^6$ cells/ml (FIG. 3g), which implies that the new network more efficiently supported metabolic activities of encapsulated cells per unit volume of the PEG matrices.

Figure 4:
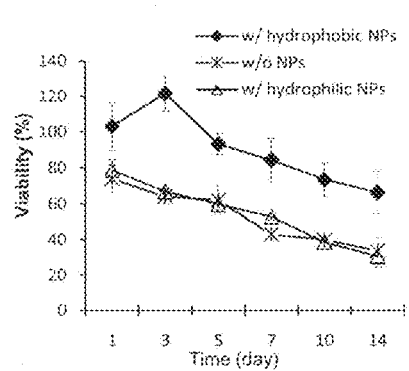
FIG. 4. (a) Samples containing hydrophilic NPs (785±6 nm diameter) had no statistically significant viability change compared to samples without NPs (p-value>0.05). (b) The difference in degradability potential between 50/50 PLGA NPs and 85/15 PLGA NPs did not lead to a significant change in associated Huh 7.5 cell viability (p-value>0.05). (c) The difference in size did not cause significant change in cell viability (p-value>0.05) (d) NP concentration of 0.01% (w/v) was used for all other samples. In order to address the NP concentration effect, we changed the NP concentration to 0.001% (w/v) or 0.1% (w/v). At 0.001% (w/v) NP concentrations, there was no significant difference between samples without NPs (p-value>0.05). Samples with 0.1% (w/v) NPs had improved viability than samples with 0.01% (w/v) NPs (p-value<0.05). (e) Particles with different levels of hydrophobicity were incorporated. Poly(dimethylsiloxane) (PDMS) has higher hydrophobicity than PLGA, evaluated by water contact angles of PDMS (118±2°) and PLGA (80±4°). PDMS microparticles had 2.4±1 μm diameter. Even though the same amount of PDMS particles had much smaller interfacial surface than PLGA NPs, there was significant improvement in cell viability of PDMS particle-containing samples compared with PLGA NP-containing samples (FIG. 5e, p-value<0.05).
Figure 4:
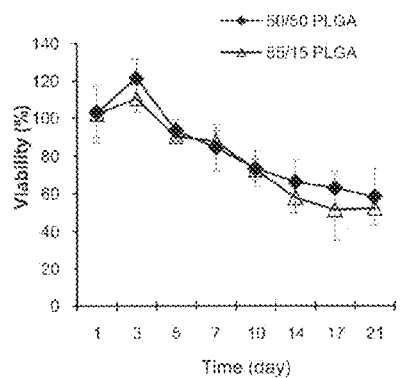
Figure 4:
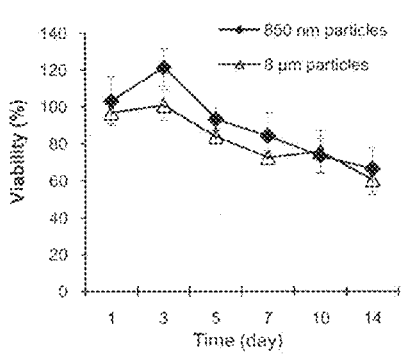
Figure 4:
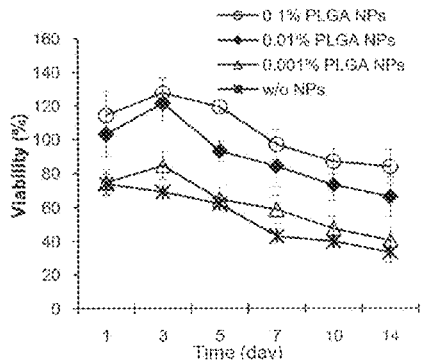
Figure 4:
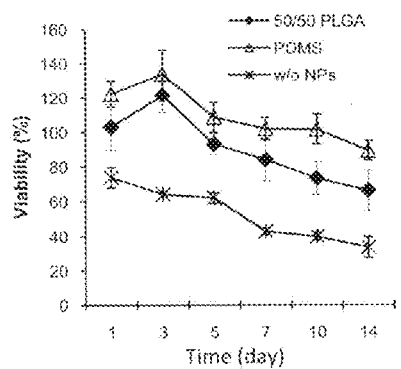

We evaluated the effects of different types of NPs to determine the most important parameter for improved viability of encapsulated cells (FIG. 4). When hydrophilic NPs were incorporated, there was no significant difference in cell viability compared to samples without NPs (FIG. 4a, p-value>0.5). To assess the effect of degradability potential of the incorporated NPs, we incorporated both 85/15 PLGA NPs (composed of 85/15 molar ratio of glycolide units and lactide units) and 50/50 PLGA NPs into the matrices and compared the viabilities. 85/15 PLGA is fully degraded around 5 or 6 months in aqueous condition, while it takes 1 or 2 months for 50/50 PLGA to be fully degraded. We measured cell viability up to 21 days at which point 50/50 PLGA loses approximately 70% of its original weight while 85/15 PLGA loses less than 10% of its original weight. Thus, the difference in degradability potential did not significantly affect cell viability (FIG. 4b, p-value>0.05).

We also prepared larger particles with an average diameter of 8.0±1.4 μm and compared their contribution to cell viability with the smaller NPs. Again, we did not observe any significant differences between the two sample groups (FIG. 4c, p-value>0.05).

The NP concentration could be another important factor affecting permeability of PEG matrices. We had used 0.01% (w/v) NP concentration in other experiments and prepared samples with different NP concentrations from 0.001% (w/v) to 0.1% (w/v) while avoiding NP aggregation. Samples with 0.001% (w/v) NP concentration had no significant effect compared to samples without NPs (FIG. 4d, p-value>0.05). However, samples with 0.1% (w/v) NPs showed increased viability compared to samples with 0.01% (w/v) NPs (FIG. 4d, p-value<0.05). Finally, we used NPs with higher hydrophobicity. We prepared poly(dimethylsiloxane) (PDMS) particles (2.4±1 μm diameter), because PDMS had a water contact angle of 118±2°, much higher than the PLGA's (80±4°), indicating higher hydrophobicity. We found significant improvement in cell viability of PDMS particle-containing samples (p-value<0.05). Taken together, these results indicate that the hydrophobicity of PLGA NPs is the primary factor contributing to the improvement in encapsulated cell viability.

In the preceding experiments studying various encapsulating conditions, we mainly used Huh 7.5, a hepatoma cell, which is widely used in hepatitis C virus (HCV) research to overcome the limited replication capabilities of other liver-derived cells. This is because it is typically difficult to maintain primary human hepatocytes in standard in vitro culture in which they rapidly lose features of advanced differentiation. There has been an attempt to encapsulate rat primary hepatocytes in PEG matrices, but the viability was too poor to perform biological assays. Thus, there needs to be a better cell-encapsulation system for the 3D culture of primary hepatocytes in order to fully benefit from the potential advantages offered by PEG hydrogels.

Figure 5:
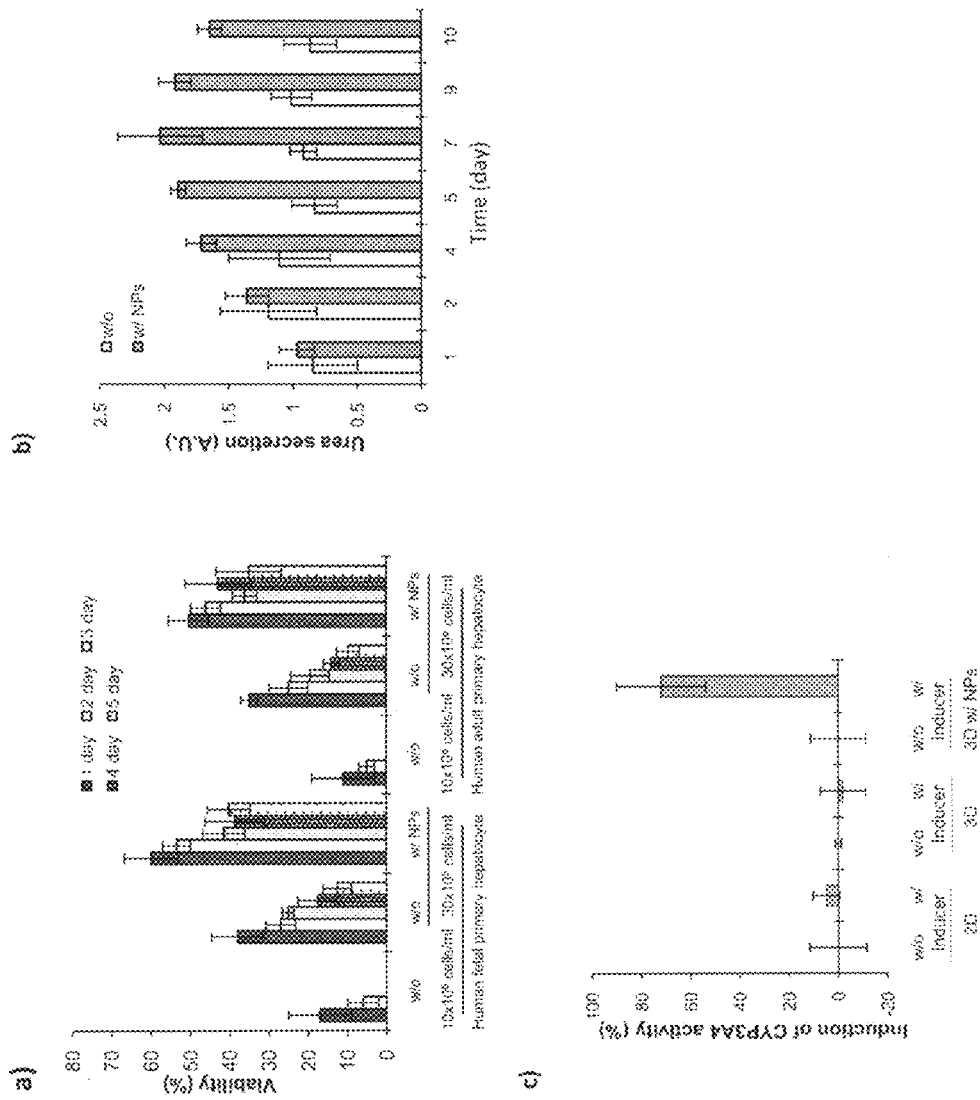
FIG. 5. (a) For human primary hepatocytes, we determined the optimal cell density to be $30 \times 10^6$ cells/ml. The addition of PLGA NPs led to further improvement of the viability of human fetal primary hepatocytes (p-value<0.01) and human adult primary hepatocytes (p-value<0.01). (b) Urea secretion from human adult primary hepatocytes was used as a hepatic function marker and normalized by cell viability. Increases in normalized urea secretion were observed for PLGA NP-incorporated samples (p-value>0.001). (c) The CYP3A4 expression levels of human adult primary hepatocytes were measured and normalized by each sample's viability. Induction of CYP3A4 activity of human adult primary hepatocytes was lost for 2D (cultured on collagen-coated plates with 100% confluency, p-value>0.05) and 3D samples without NPs (encapsulated in PEG hydrogels without PLGA NPs, p-value>0.05). However, there was significant restoration of the induction of CYP3A4 activity in 3D samples with NPs (encapsulated in PLGA nanoparticle-incorporated hydrogels, p-value<0.01).

Due to the resistance to cell attachment to the PEG network and the anchor dependence of liver-derived cells, we conjugated RGD (Arg-Gly-Asp) peptides, a cell binding domain, to PEG network for human primary hepatocyte encapsulation. We observed that human primary hepatocytes required much higher cell densities than Huh 7.5 cells and determined the optimal cell density to be $30 \times 10^6$ cells/ml for cell viability (FIG. 5a). To test the benefit of incorporating PLGA NPs, we measured the viabilities of different sample groups. As expected, there were significant improvements in viability for NP-containing samples (FIG. 5a, p-value<0.001 for both fetal and adult primary hepatocytes).

Since our approach was designed to improve phenotype stability by increasing matrix permeability, we selected urea as a hepatic function marker because the diameter (less than 0.5 nm) is small enough not to be trapped by the network. We verified that there was no significant difference in urea diffusion between samples with and without PLGA NPs. As expected, we observed significant increases in urea secretion, normalized by each sample's viability, in the samples with PLGA NPs (FIG. 5b, p-value<0.01).

We also measured the induction activity of cytochrome P-450 monooxygenase 3A4 (CYP3A4). CYP3A4 is involved in the oxidative metabolism of various xenobiotics, including more than 50% of clinically used drugs. The expression level of this enzyme is related to the accumulation of toxic metabolites, drug side effects, and the therapeutic efficacy of a coadministered drug. The induction activity of CYP3A4 was evaluated by the relative expression level of the enzyme between samples cultured with and without inducers, which avoids permeability effects between samples. We tested induction of CYP3A4 activity to rifampicin, a bactericidal antibiotic drug of the rifamycin group, which is known to be one of the most reliable CYP3A4 inducers. We used human adult primary hepatocytes from two donors that had lost the CYP3A4 induction activity when they were cultured on collagen-coated 2D tissue culture plates (FIG. 5c, p-value>0.05). Even though the cells in 3D matrices without NPs showed no response to the inducer (FIG. 5c, p-value>0.05), we observed restored induction activity of CYP3A4 in NP-containing samples (FIG. 5c, p-value<0.01). Taken together, these results show that incorporation of hydrophobic NPs is an effective way to improve phenotype stability of encapsulated cells.

New network design maintains patternability of cell-encapsulated PEG hydrogels. One of the critical features of engineered tissue scaffolds is the replication of in vivo geometry and dimensional size scale in order to provide an environment that can guide cell behavior with respect to morphology, cytoskeletal structure, and functionality. In order to obtain more reliable microscale architectures within a PEG matrix, there should be appropriate mechanical strength for long term structural stability, and the viscosity of the fluid prepolymer needs to be low enough for the prepolymer to flow into microscale structures to allow fabrication through soft lithography or microfluidic processing. However, because the diffusion condition in a PEG-based scaffold is the primary factor for phenotype stability of encapsulated cells, it is a challenge to design a network to satisfy these contradictory requirements. Since our new network design for improving the hydrogel permeability was intended to partially induce loose crosslinking only at the particle-PEG interface, we expected that this approach would minimize loss of physical properties for patternability.

In order to evaluate the patternability, we measured the viscosity of the prepolymer and compression modulus of the cured matrices. As the macromonomer molecular weight increased from 3.4 k to 8 k, the viscosity increased (306±3%) and the compression modulus of the cured gel decreased (77±4%), as shown in FIG. 6a. Because 8 k PEG matrices had similar cell viability as for 3.4 k PEG matrices, as shown in FIG. 1e, network design based on ideal network mesh size was not appropriate. In sharp contrast, PLGA NP-containing samples had no significant change in the viscosity of prepolymer solution (p-value>0.05) and minimum loss for the gel compression modulus (31±3%) (FIG. 6a). The maintained patternability adds to the benefits of increased cell viability and functionality that we have already illustrated in earlier sections.

In making use of the structural advantage of our network design, we attempted to control the spatial distribution of incorporated cells within cell-encapsulated PEG. In many tissues, different types of cells distribute with specific configurations, and their interactions are of fundamental importance in physiology, pathophysiology, oncology, developmental biology, and wound healing. In the actual liver, for example, hepatocytes are aggregated in sheets and separated by blood channels, called sinusoids. The proper distribution of non-parenchymal cells along the sinusoid is a prerequisite to restore various functions of the liver. Several approaches have been successfully proposed to restore heterotypic interactions by stacking PEG matrix layers of different cell types.

We sought a method to guide cells' spatial displacement with a more simplified patterning process, which is given in FIG. 6b. We used a soft lithography approach to control the geometry and dimensions of encapsulated cells in PEG matrices. We first fabricated the desired microstructure in a silicon wafer and transferred it to a poly(dimethylsiloxane) (PDMS) replica. We then cured cell-containing PEG prepolymer between the PDMS replica and a glass slide. In curing the prepolymer, we transferred the microstructure of the PDMS replica to the cured PEG matrices. We observed no further negative influence on cell viability during the patterning process. This became possible due to the minimum change in viscosity of the prepolymer. Because the loss of mechanical strength was minor, the patterned structure was also maintained for more than one month. The microstructure was designed to control the spatial distribution of encapsulated cells and to trap other types of cells within the patterned, depressed regions on the surface of cell-encapsulated PEG matrices. On the surface of the PEG hydrogel, we deposited fibronectin, which is known to physically attach on a hydrogel surface with long term stability. Then a second type of cells was loaded along the depressed region (FIG. 6c).

Using the new platform, we attempted to address how spatial distribution of two different cell types affects their functions. Since the incorporation of hydrophobic NPs was verified to improve homotypic interactions, we reasoned that we might be able to achieve an even more desirable 3D environment for the encapsulated cells by providing a second cell type on the surface, thus providing both homotypic and heterotypic cellular interactions, as present in many tissues. Because cellular interaction between hepatocytes and fibroblasts has been well-investigated and is known to enhance hepatic functions, we selected fibroblasts for incorporation into our system. It has been reported that cellular interactions between hepatocytes and fibroblasts are initiated only by direct contact-mediated signals, but they could be maintained within a short range (~325 µm) by soluble signals. Thus, even after the fibroblasts had been exchanged with naïve fibroblasts that hadn't been in direct contact with hepatocytes, the hepatocytes could maintain the initiated interaction with the naïve fibroblasts by soluble signals. In order for encapsulated hepatocytes to interact with fibroblasts on the matrix surface, we first co-cultured human adult primary hepatocytes with NIH 3T3 fibroblasts for 2 days and encapsulated both cell types into PEG matrices. Then NIH 3T3 fibroblasts were loaded on the matrix surface. Because we had verified that increased interaction with fibroblasts led to increased secretion of urea and albumin from hepatocytes, the cellular interaction between encapsulated hepatocytes and fibroblasts on the matrix surface could be evaluated by the secreted amounts of these hepatic function markers. In our system, the cellular interaction between two types of cells could be reliably regulated by controlling cell numbers on the matrix surface at specific configurations. In FIG. 6c, all samples had the same number of encapsulated hepatocytes and fibroblasts, and Type 2 and Type 3 had twice as many fibroblasts on the surface compared to Type 1.

It took several days for the two types of cells to establish stable heterotypic interactions, so we waited five days after encapsulation before we started examining the secretion of hepatic markers. Because all the samples had incorporated PLGA NPs, we could ignore permeability differences among samples. As expected, increased numbers of fibroblasts on the matrix surface led to enhanced secretion of urea, as shown in comparison between samples without fibroblasts on the matrix surface vs. sample Type 1 (FIG. 6d, p-value<0.05), and between Type 1 vs. Type 2 (FIG. 6d, p-value<0.001). We also observed that different configurations of patterned cells on the matrix surface resulted in different levels of urea secretion, as shown in comparison of Type 2 and Type 3 (FIG. 6d, p-value<0.001). Because the interaction between encapsulated hepatocytes and fibroblasts was mediated by soluble signals, we suggest that the increased urea secretion for Type 3 compared to Type 2 could be due to a more favorable surface configuration in Type 3, in which fibroblasts were well-distributed through the surface so that soluble signals could be delivered to more encapsulated cells. We also compared albumin secretion from each sample group and found similar trends in which increasing number of fibroblasts on the surface improved albumin secretion. Even though this experiment was designed only to provide a qualitative evaluation of heterotypic interactions, this approach provides a platform to understand how distributions of different types of cells and their consequent interactions affect various biological responses.

Network defects serve as an important parameter in modifying the physical configuration of a cell-encapsulated PEG network. We incorporated hydrophobic NPs to augment network defects by purposefully inducing loose crosslinking at the particle-PEG interface. This approach was verified to be an effective way to satisfy the seemingly contradictory requirements for an optimal network; it improved the permeability to support metabolic activities of cell-encapsulated PEG matrices while maintaining patternability by minimizing the loss of mechanical strength and viscosity. This structural advantage allowed us to construct micron-scale cell-trapping architectures for the encapsulated cells to potentially restore heterotypic cellular interactions akin to native tissues. We expect that this strategy to design network structures of cell-encapsulated hydrogels can be applied to restore more natural 3D environments of many tissues with complicated architectures.

Methods

Synthesis of PEG diacrylate (PEG-DA). PEG-DA was synthesized as described previously (Myung et al. (2007) Polymer 48(18):5376-5387). Briefly, 10 g of PEG macromers (3.4 k or 8 k MW, Sigma-Aldrich) were dissolved in 100 ml of anhydrous tetrahydrofuran (THF, Sigma-Aldrich) at 50° C. Then, a 15-fold molar excess of acryloyl chloride (Sigma-Aldrich) over PEG was added to the reaction flask and left to react for 5 hours under a nitrogen atmosphere. After it cooled to room temperature, the reaction flask was left in a 4° C. refrigerator overnight to allow the PEG-DA to crystallize. The THF solution was then removed, and 100 mL of fresh THF was added to dissolve the crystallized PEG-DA in the reaction flask with water (50° C.). In order to completely remove residual reagents, we performed the PEG-DA recrystallization four times. It was then dried in an oven (30° C.) to evaporate the residual THF, after which the PEG-DA powder was collected.

RGD-conjugation to PEG. To synthesize RGD-conjugated PEG, acryloyl-PEG-Arg-Gly-Asp-Cys (Acr-PEG-RGDC) was prepared as previously described (Hem et al. (1998) J. Biomed. Mater. Res. 39(2):266-276). Briefly, Arg-Gly-Asp-Cys (RGDC) (American Peptide) was dissolved at 1 mg/mL in 50 mM sodium bicarbonate buffer (pH 8.2) and reacted with an equimolar amount of acryloyl-PEG-N-hydroxysuccinimide (3400 Da, Laysan Bio, Inc) for 2 hours at room temperature and then lyophilized.

Preparation of Hydrophobic Particles of Poly(lactic-Co-Glycolic Acid) (PLGA) and poly(dimethylsiloxane) (PDMS) particles. We prepared different types of particles. The PLGA NPs were prepared by the spontaneous emulsification solvent diffusion method (Niwa et al. (1993) J. Controlled Release 25(1-2):89-98). A solution of 1% (w/v) 50/50 PLGA (composed of 50/50 molar ratio of glycolide units and lactide units, 85 k molecular weight, LACTEL) in a mixture of dichloromethane (DCM, Sigma-Aldrich) and acetone (Sigma-Aldrich) (8:2, v/v) was poured into 100 times its volume of phosphate buffered saline (PBS, Cellgro). The solution was emulsified for 2 min at ~30,000 rpm using a PRO200 Laboratory Homogenizer (Pro Scientific). Acetone in the organic mixture diffused rapidly into the aqueous solution and reduced the interfacial tension between the organic and the aqueous solution, which resulted in the organic solution forming fine droplets. The emulsion was stirred at 1,000 rpm overnight at room temperature and atmospheric pressure to allow DCM to evaporate. The final concentration of PLGA NPs was 0.01% (w/v) in PBS. The average diameter of the NPs, measured by dynamic light scattering, was 870±34 nm. We also measured the water contact angle of a PLGA film, with higher contact angle representing greater hydrophobicity. To prepare a PLGA film, dissolved PLGA in DCM was spread on a glass slide and the DCM was allowed to evaporate.

For PLGA microparticles, 50/50 PLGA (LACTEL) was dissolved in DCM at 20% (w/v) concentration. The aqueous PBS was then added to the non-aqueous PLGA solution at 20% (v/v) and emulsified for 2 min at approximately 30,000 rpm. The emulsion was poured, into 100 times its volume of PBS with 0.05% (w/v) polyvinyl alcohol) and stirred at 1,000 rpm for 3 hours at room temperature and atmospheric pressure for DCM to evaporate. The solid microspheres were obtained by centrifugation and incubated in PBS for 1 day with stirring and refreshing of PBS. Then the microspheres were collected by centrifugation and stored at −20° C. The diameters of the microparticles were 8.0±1 µm based on analysis optical microscopic images using OPENLAB image software (Improvision Inc.).

For PDMS particles, PDMS prepolymer (SYLGARD® 184 Silicone Elastomer kit, Dow Corning Corporation) was prepared by mixing the base with the curing agent in a 10:1 mass ratio and poured into 100 times the volume of water and emulsified for 1 hour. Cured particles were collected by a centrifuge. The average diameters of the microparticles were 2.4±1 µm.

Cell culture. Huh 7.5 cells were provided by Dr. Charles M. Rice (Rockefeller University) and cultured as follows.

Briefly, Huh 7.5 cell monolayers were propagated in Dulbecco's modified minimal essential medium (DMEM) (Cellgro) in the presence of 10% fetal bovine serum (Omega Scientific), 2 mM L-glutamine (Cellgro), 100 IU/ml penicillin, 100 μg/ml streptomycin (Cellgro), and 0.1 mM nonessential amino acids (GIBCO). Huh 7.5 cells were grown in cell culture dishes at 37° C. with 5% $CO_2$.

Human fetal primary hepatocytes were isolated and purified from human fetal liver obtained under approved protocol from Advanced Biosciences Research Inc., as described previously. Briefly, the liver tissue was minced, digested with 0.1% collagenase H (Roche Applied Science) and 1 mg/ml DNAse I (Invitrogen) in Hank's Balanced Salt Solution (HBSS, Sigma-Aldrich) for 20 min at 37° C., and then filtered through a 70 μm nylon mesh (Sigma-Aldrich). This process was repeated two or three times with filtered pieces of the tissue, and cell suspensions were achieved. The suspensions were centrifuged at 30 g for 5 min, and the fetal liver cells at the bottom were collected, while floating red blood cells were depleted.

Human adult primary hepatocytes were purchased from CellzDirect, Inc. The human primary hepatocytes were suspended in DMEM/F-12 (Invitrogen), supplemented with ITS+ premix (BD Pharmingen), $10^{-7}$ M of dexamethasone (Sigma-Aldrich), 10 mM of nicotinamide (Sigma-Aldrich), 0.5 mM of ascorbic acid 2-phosphate (Sigma-Aldrich), 4 mM of L-glutamine (Invitrogen), 0.1 mg/ml of heparin (Sigma-Aldrich), 5% FBS (Sigma-Aldrich), 100 U/ml Penicillin G (Sigma-Aldrich) and Streptomycin (Invitrogen), and 20 ng/ml of epithelial growth factor (EGF) (Sigma-Aldrich). Cells were cultured in collagen-coated cell culture dishes (BD Biosciences) at 37° C. with 5% $CO_2$.

Cell encapsulation in PEG matrices. PEG-DA was dissolved in PBS with 0.05% (w/v) of the photoinitiator, Irgacure 2959 (Ciba). Hydrophobic PLGA NPs were added to the solution for some samples with the designated concentrations. For hydrophilic particles, we used 785±6 nm diameter polystyrene beads (Polybead® Carboxylate 0.75 Micron Microspheres, Polysciences) that had been surface-modified with carboxyl groups. The cell suspension was then added to a given PEG-DA prepolymer solution. The final prepolymer solution was loaded between glass slides (VWR) separated by a Teflon spacer (250 μm, 500 μm, 725 μm, or 1,000 μm thick) and exposed to 320-390 nm UV light with 10 mW/cm$^2$ intensity (Cure spot 50, DYMAX) for 47 seconds. The cured hydrogels were subsequently washed with PBS and then cultured in non-tissue-culture-treated multi-well plates with cell culture medium; the medium was changed daily. For primary hepatocyte encapsulation, RGD-conjugated PEG was mixed with the prepolymer at 20 μmol/ml.

Measuring cell viability in 3D samples by combining Alamar Blue® assays and Live/Dead® assay. Most cell viability assays have been developed for cells in 2D culture dishes, and it is difficult to apply them directly to 3D samples. For the measurement of cell viability in 3D samples, it is common practice to manually count live/dead cells, stained by the Live/Dead® assay, but it is not practical when there are numerous parameters to be measured, as in our experimental design. To address this, we adapted a modified cell viability method for 3D samples. Briefly, relative cell viabilities of all samples at each time point were measured by the Alamar Blue® assay. For each set of experiments, we determined a reference sample group and manually counted live and dead cells stained by the Live/Dead® assay to compare viability changes between each time point. By combining data from the two assays, we generated a modified viability parameter to show the general trend of cell viability for all 3D samples.

Measurement of compression modulus and viscosity. For measuring compression modulus, hydrogel samples without encapsulated cells were prepared under the same conditions as for the cell-encapsulation, except for the existence of cells. The specimens had 50 mm diameter with 250 μm thickness. The compression modulus for each sample group was calculated as an average of triplicate uniaxial compression tests using an Instron 5844 materials testing apparatus. The viscosities of different aqueous PEG solutions were measured at room temperature (23° C.) and pressure by using a rheometer (AR 2000 Rheometer, TA instruments).

Measuring amount of urea and albumin. The urea and albumin secretions from encapsulated cells were measured as follows. Briefly, cell culture media samples were collected and held at −20° C. until processing. Urea and albumin in the culture medium were measured by Urea Nitrogen Test kit (Stanbio) and Albumin Blue Fluorescent Assay Kit (Active Motif), respectively.

Measuring induction of CYP3A4 activity. One day after cell encapsulation, a well-known inducer, rifampin, was added in cell culture medium at 20 μg/mg, and cultured 48 hours. The cell culture medium was changed daily. Subsequently, the induction of CYP3A4 activity was measured by P450-Glo™ CYP3A4 assay kit (Promega).

Cell patterning within cell-encapsulated PEG matrices. Microstructures in silicon wafers were prepared by standard microfabrication processing techniques. We created structures 200 μm deep by using the STS Deep RIE Etcher (Surface Technology Systems). The microstructures could be transferred to poly(dimethylsiloxane) (PDMS) replicas by curing PDMS prepolymer (SYLGARD® 184 Silicone Elastomer kit, Dow Corning Corporation) for 30 minutes at 70° C. over the silicon wafer. Cell-containing PEG prepolymer was cured between the PDMS replicas and a glass slide. Cell culture media with fibronectin at 30 μg/mL was then loaded on the surface of the cured PEG matrices for 1 hour and washed with PBS. The second type of cells was loaded within the microstructure on the PEG matrix surface. By generating slight agitation or flow, loaded cells were stably entrapped within the patterned depressions where less shear stress was applied. After allowing one hour for cells to attach, unattached cells were removed by rinsing with cell culture media, and the matrices were incubated under normal cell culturing conditions. To obtain images of patterned cells, encapsulated cells were stained red by DiI (Vybrant™ Cell-Labeling Solutions, Molecular Probes®), and patterned cells were stained green by DiO (Vybrant™ Cell-Labeling Solutions, Molecular Probes®).

Statistical analysis. Statistical analysis was performed using ANOVA, unless otherwise specified. Experiments done with Huh 7.5 cells had n≥6, and experiments done with human primary hepatocytes had n=3. Statistical differences between sample groups were calculated within overall time points, not at one time point. All values are reported as the mean and standard deviation of the mean.

What is claimed is:

1. A cellular composition comprising:
   viable liver cells encapsulated in a high permeability hydrogel with network defects resulting from introduction of hydrophobic nanoparticles;
   wherein the composition is formed by combining in a precursor solution polyethylene glycol (PEG) diacrylate with poly(lactic-co-glycolic acid) (PLGA) nanoparticles, in the presence of viable liver cells and a polymerization initiator,
   wherein the diameter of the nanoparticles is from about 100 nm to about 100 μm diameter; and wherein the concentration of the nanoparticles is from 0.01% to 1% weight/volume of the precursor solution.

2. The composition of claim 1, wherein the hydrogel comprises biologically active peptides or proteins.

3. The composition according to claim 2, wherein the biologically active peptides or proteins are linked to PEG.

4. The composition of claim 1, wherein the viable liver cells are primary cells.

5. The composition according to claim 1, wherein the hydrogel is patterned into a nanostructure prior to polymerization.

6. The composition of claim 1, wherein the polymerization initiator is a photoinitiator.

7. A pharmaceutical formulation comprising a composition according to claim 1; and
a pharmaceutically acceptable excipient.

8. The cellular composition of claim 1, wherein the PEG diacrylate has a molecular weight of at least 2.5 K and not more than 20 K.

9. The cellular composition of claim 1, wherein the PEG diacrylate is present in the precursor solution at a concentration of at least 7.5% and not more than 30%.

* * * * *